United States Patent
Belson (10) Patent No.: US 11,051,988 B2
(45) Date of Patent: Jul. 6, 2021

(54) METHODS AND APPARATUS FOR INHIBITING SCAR FORMATION

(71) Applicant: ZipLine Medical, Inc., Campbell, CA (US)

(72) Inventor: Amir Belson, Savyon (IL)

(73) Assignee: Zipline Medical, Inc., Campbell, CA (US)

( * ) Notice: Subject to any disclaimer, the term of this patent is extended or adjusted under 35 U.S.C. 154(b) by 220 days.

(21) Appl. No.: 16/177,101

(22) Filed: Oct. 31, 2018

(65) Prior Publication Data

US 2019/0060128 A1    Feb. 28, 2019

Related U.S. Application Data

(60) Division of application No. 13/685,909, filed on Nov. 27, 2012, now abandoned, which is a continuation of
(Continued)

(51) Int. Cl.
*A61F 13/00* (2006.01)
*A61F 13/02* (2006.01)
(Continued)

(52) U.S. Cl.
CPC ............ *A61F 13/02* (2013.01); *A61B 17/085* (2013.01); *A61F 13/023* (2013.01); *A61B 2017/00557* (2013.01)

(58) Field of Classification Search
CPC ....... A61B 17/08; A61B 17/085; A61B 17/22; A61B 2017/22051; A61B 2017/22065;
(Continued)

(56) References Cited

U.S. PATENT DOCUMENTS 2,012,755 A    8/1935   Muth
2,371,978 A    3/1945   Perham
(Continued)

FOREIGN PATENT DOCUMENTS

CN    1126430 A    7/1996
CN    1442119 A    9/2003
(Continued)

OTHER PUBLICATIONS

"Notice of Allowance dated Jun. 15, 2018 for U.S. Appl. No. 13/665,160."
(Continued)

*Primary Examiner* — Victoria J Hicks
(74) *Attorney, Agent, or Firm* — McDonnell Boehnen Hulbert & Berghoff LLP (57) ABSTRACT

Scar formation is inhibited by simultaneously applying a vertical force and a lateral compression to the wound site during the healing process. Apparatus for applying such simultaneous forces can include a backing and a tissue displacement device. The backing holds the tissue displacement device over the wound. The tissue displacement device may be expanded to both apply the vertical force against the wound and to draw the backing radially or laterally inward to apply the desired compression forces to the wound.

20 Claims, 3 Drawing Sheets

Related U.S. Application Data application No. PCT/US2011/040213, filed on Jun. 13, 2011.

(60) Provisional application No. 61/397,604, filed on Jun. 14, 2010.

(51) Int. Cl.
*A61B 17/08* (2006.01)
*A61B 17/00* (2006.01)

(58) Field of Classification Search
CPC  A61B 2017/22067; A61B 2017/22068; A61B 2017/22069; A61B 2017/22071; A61B 2017/00535; A61B 2017/00557; A61B 2017/081; A61B 17/083; A61B 2017/086; A61B 2017/088; A61F 5/34; A61F 5/30; A61F 5/32; A61F 2007/0091; A61F 2007/0092; A61F 13/069; A61F 2013/0017; A61F 2013/00174; A61F 13/02; A61F 13/023
USPC .......................... 602/53; 606/201, 202, 204
See application file for complete search history.

(56) References Cited

U.S. PATENT DOCUMENTS

| | | |
|---|---|---|
| 2,747,248 A | 5/1956 | Mercer |
| 3,118,201 A | 1/1964 | Raymond, Jr. |
| 3,487,836 A | 1/1970 | Benjamin et al. |
| 3,516,409 A | 6/1970 | Robert |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,971,384 A | 7/1976 | Hasson |
| 3,972,328 A | 8/1976 | Chen |
| 3,983,878 A | 10/1976 | Kawchitch |
| 4,038,989 A | 8/1977 | Romero-Sierra et al. |
| 4,114,624 A | 9/1978 | Haverstock |
| 4,210,148 A | 7/1980 | Stivala |
| 4,222,383 A | 9/1980 | Schossow |
| 4,224,945 A * | 9/1980 | Cohen .................. A61F 5/34 602/53 |
| 4,526,173 A | 7/1985 | Sheehan |
| 4,531,521 A | 7/1985 | Haverstock |
| 4,535,772 A | 8/1985 | Sheehan |
| 4,539,990 A | 9/1985 | Stivala |
| 4,576,163 A | 3/1986 | Bliss |
| 4,605,005 A | 8/1986 | Sheehan |
| 4,612,230 A | 9/1986 | Liland et al. |
| 4,676,245 A | 6/1987 | Fukuda |
| 4,702,251 A | 10/1987 | Sheehan |
| 4,780,168 A | 10/1988 | Beisang et al. |
| 4,871,367 A | 10/1989 | Christensen et al. |
| 4,881,546 A | 11/1989 | Kaessmann |
| 4,905,694 A | 3/1990 | Will |
| 4,950,282 A | 8/1990 | Beisang et al. |
| 4,966,605 A | 10/1990 | Thieler |
| 4,976,726 A | 12/1990 | Haverstock |
| 5,176,703 A | 1/1993 | Peterson |
| 5,190,032 A | 3/1993 | Zacoi |
| 5,259,835 A | 11/1993 | Clark et al. |
| 5,306,236 A | 4/1994 | Blumenfeld et al. |
| 5,336,219 A | 8/1994 | Krantz |
| 5,377,695 A | 1/1995 | An Haack |
| 5,514,155 A * | 5/1996 | Daneshvar ......... A61B 17/1325 128/118.1 |
| 5,533,519 A | 7/1996 | Radke et al. |
| 5,562,705 A | 10/1996 | Whiteford |
| 5,665,108 A | 9/1997 | Galindo |
| 5,725,507 A | 3/1998 | Petrick |
| 5,788,660 A | 8/1998 | Resnik |
| 5,823,983 A | 10/1998 | Rosofsky et al. |
| 5,843,123 A | 12/1998 | Brazeau |
| 6,007,564 A | 12/1999 | Haverstock |
| 6,033,654 A | 3/2000 | Stedronsky et al. |
| 6,074,965 A | 6/2000 | Bodenschatz et al. |
| 6,126,615 A | 10/2000 | Allen et al. |
| 6,176,868 B1 | 1/2001 | Detour |
| 6,194,629 B1 | 2/2001 | Bernhard |
| 6,629,949 B1 | 10/2003 | Douglas |
| 6,689,100 B2 | 2/2004 | Connelly et al. |
| 6,726,706 B2 | 4/2004 | Dominguez |
| 7,066,182 B2 | 6/2006 | Dunshee |
| 7,361,185 B2 | 4/2008 | O'Malley et al. |
| 7,455,681 B2 | 11/2008 | Wilke et al. |
| 7,511,185 B2 | 3/2009 | Lebner |
| 7,641,682 B2 | 1/2010 | Palmaz et al. |
| 7,645,285 B2 | 1/2010 | Cosgrove et al. |
| 7,799,042 B2 | 9/2010 | Williamson, IV et al. |
| 8,246,590 B2 | 8/2012 | Hu et al. |
| 8,313,508 B2 | 11/2012 | Belson et al. |
| 8,323,313 B1 | 12/2012 | Belson et al. |
| 8,439,945 B2 | 5/2013 | Belson et al. |
| 8,592,640 B2 | 11/2013 | Zepeda et al. |
| 8,663,275 B2 | 3/2014 | O'Malley et al. |
| 9,008,784 B2 | 4/2015 | Chan et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,271,858 B2 | 3/2016 | Ben-Meir et al. |
| 9,474,529 B2 | 10/2016 | Belson et al. |
| 9,554,799 B2 | 1/2017 | Belson et al. |
| 9,554,800 B2 | 1/2017 | Belson et al. |
| 9,561,034 B2 | 2/2017 | Belson et al. |
| 9,642,621 B2 | 5/2017 | Belson et al. |
| 9,642,622 B2 | 5/2017 | Belson et al. |
| 10,010,710 B2 | 7/2018 | Belson et al. |
| 10,123,800 B2 | 11/2018 | Belson et al. |
| 10,123,801 B2 | 11/2018 | Belson et al. |
| 10,159,825 B2 | 12/2018 | Belson et al. |
| 2002/0099315 A1 | 7/2002 | Lebner |
| 2003/0065294 A1 | 4/2003 | Pickup et al. |
| 2003/0108352 A1 | 6/2003 | Hellman |
| 2003/0120198 A1 | 6/2003 | Barkell et al. |
| 2003/0163160 A1 | 8/2003 | O'Malley et al. |
| 2003/0220596 A1 | 11/2003 | Dunshee |
| 2004/0072964 A1 | 4/2004 | Udding et al. |
| 2004/0106904 A1 | 6/2004 | Gonnelli et al. |
| 2004/0204740 A1 | 10/2004 | Weiser |
| 2004/0210176 A1 | 10/2004 | Diana |
| 2004/0260234 A1 | 12/2004 | Srinivasan et al. |
| 2005/0020956 A1 | 1/2005 | Lebner |
| 2005/0020957 A1 | 1/2005 | Lebner |
| 2005/0070956 A1 | 3/2005 | Rousseau |
| 2005/0080453 A1 | 4/2005 | Lebner et al. |
| 2005/0085757 A1 | 4/2005 | Santanello |
| 2005/0153090 A1 | 7/2005 | Marchitto et al. |
| 2005/0234485 A1 | 10/2005 | Seegert et al. |
| 2005/0277959 A1 | 12/2005 | Cosgrove et al. |
| 2005/0284801 A1 | 12/2005 | Tacklind |
| 2006/0030886 A1 | 2/2006 | Clark |
| 2006/0122522 A1 | 6/2006 | Chavan et al. |
| 2006/0200198 A1 | 9/2006 | Riskin et al. |
| 2006/0259033 A1 | 11/2006 | Nesbitt |
| 2007/0026078 A1 | 2/2007 | Almarsson et al. |
| 2007/0038247 A1 | 2/2007 | Lebner et al. |
| 2007/0078366 A1 | 4/2007 | Haggstrom et al. |
| 2007/0088339 A1 | 4/2007 | Luchetti et al. |
| 2007/0106277 A1 | 5/2007 | Hood et al. |
| 2007/0141130 A1 | 6/2007 | Villanueva et al. |
| 2007/0179419 A1 | 8/2007 | Simpson |
| 2007/0185432 A1 | 8/2007 | Etheredge, III |
| 2007/0260278 A1 | 11/2007 | Wheeler et al. |
| 2008/0033334 A1* | 2/2008 | Gurtner ................ A61L 15/58 602/50 |
| 2008/0069855 A1 | 3/2008 | Bonutti |
| 2008/0081951 A1 | 4/2008 | Frasier et al. |
| 2008/0103550 A1 | 5/2008 | Wenzel et al. |
| 2008/0114396 A1 | 5/2008 | Cory et al. |
| 2008/0147115 A1 | 6/2008 | O'Malley et al. |
| 2008/0161731 A1 | 7/2008 | Woods et al. |

(56) References Cited

U.S. PATENT DOCUMENTS

| | | |
|---|---|---|
| 2008/0228219 A1 | 9/2008 | Weiser |
| 2008/0287864 A1 | 11/2008 | Rosenberg |
| 2009/0036922 A1 | 2/2009 | Riskin et al. |
| 2009/0062531 A1 | 3/2009 | Kanda |
| 2009/0099496 A1 | 4/2009 | Heegaard et al. |
| 2009/0149869 A1 | 6/2009 | Lhun |
| 2009/0158131 A1 | 6/2009 | Choi et al. |
| 2009/0162531 A1 | 6/2009 | Nesbitt |
| 2009/0177225 A1 | 7/2009 | Nunez et al. |
| 2009/0177227 A1 | 7/2009 | Warren |
| 2009/0264709 A1 | 10/2009 | Blurton et al. |
| 2009/0299255 A1 | 12/2009 | Kazala, Jr. et al. |
| 2009/0299257 A1 | 12/2009 | Long et al. |
| 2009/0299303 A1* | 12/2009 | Seegert ............ A61F 13/00017 604/290 |
| 2010/0036209 A1 | 2/2010 | Ferren et al. |
| 2010/0100022 A1 | 4/2010 | Greener et al. |
| 2010/0121286 A1 | 5/2010 | Locke et al. |
| 2010/0228287 A1 | 9/2010 | Jeekel et al. |
| 2010/0280545 A1 | 11/2010 | Fridman |
| 2011/0077667 A1 | 3/2011 | Singhatat et al. |
| 2011/0106026 A1 | 5/2011 | Wu et al. |
| 2011/0118698 A1 | 5/2011 | Eckhoff et al. |
| 2011/0144470 A1 | 6/2011 | Mazar et al. |
| 2012/0016410 A1 | 1/2012 | Belson et al. |
| 2012/0029266 A1 | 2/2012 | Holmes et al. |
| 2012/0046691 A1 | 2/2012 | Belson et al. |
| 2012/0095502 A1 | 4/2012 | Bargon et al. |
| 2012/0116279 A1 | 5/2012 | Munro et al. |
| 2012/0116485 A1 | 5/2012 | Burgmann |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0232587 A1 | 9/2012 | Burke et al. |
| 2013/0066365 A1 | 3/2013 | Belson et al. |
| 2013/0072969 A1 | 3/2013 | Zhang |
| 2013/0108352 A1 | 5/2013 | Ruiz, Sr. et al. |
| 2013/0178897 A1 | 7/2013 | Wu et al. |
| 2013/0267928 A1 | 10/2013 | Imran et al. |
| 2013/0281885 A1 | 10/2013 | Rowbottom et al. |
| 2013/0281981 A1 | 10/2013 | Shamir |
| 2013/0282049 A1 | 10/2013 | Peterson et al. |
| 2013/0331757 A1 | 12/2013 | Belson |
| 2014/0074156 A1 | 3/2014 | Belson et al. |
| 2014/0171849 A1 | 6/2014 | Fischell et al. |
| 2014/0222070 A1 | 8/2014 | Belson et al. |
| 2014/0228712 A1 | 8/2014 | Elliott et al. |
| 2014/0278229 A1 | 9/2014 | Hong et al. |
| 2014/0316323 A1 | 10/2014 | Kanevsky et al. |
| 2015/0045700 A1 | 2/2015 | Cavanagh et al. |
| 2015/0105423 A1 | 4/2015 | Haudenschild et al. |
| 2015/0148653 A1 | 5/2015 | Fleig et al. |
| 2015/0209563 A1 | 7/2015 | Amir |
| 2015/0216527 A1 | 8/2015 | Belson et al. |
| 2015/0309535 A1 | 10/2015 | Connor et al. |
| 2015/0313593 A1 | 11/2015 | Patenaude et al. |
| 2015/0351690 A1 | 12/2015 | Toth et al. |
| 2016/0007909 A1 | 1/2016 | Singh et al. |
| 2016/0095597 A1 | 4/2016 | Belson et al. |
| 2016/0106931 A1 | 4/2016 | Belson et al. |
| 2016/0114146 A1 | 4/2016 | Belson et al. |
| 2016/0202755 A1 | 7/2016 | Connor |
| 2016/0206311 A1 | 7/2016 | Belson et al. |
| 2016/0206312 A1 | 7/2016 | Belson et al. |
| 2016/0206313 A1 | 7/2016 | Belson et al. |
| 2016/0213924 A1 | 7/2016 | Coleman et al. |
| 2016/0220175 A1 | 8/2016 | Tam et al. |
| 2016/0220252 A1 | 8/2016 | Belson et al. |
| 2016/0242646 A1 | 8/2016 | Obma |
| 2016/0249924 A1 | 9/2016 | Belson et al. |
| 2016/0296149 A1 | 10/2016 | Polsky et al. |
| 2016/0302721 A1 | 10/2016 | Wiedenhoefer et al. |
| 2016/0310140 A1 | 10/2016 | Belson et al. |
| 2017/0042541 A1 | 2/2017 | Belson et al. |
| 2017/0143341 A1 | 5/2017 | Belson et al. |
| 2017/0156664 A1 | 6/2017 | Belson et al. |

FOREIGN PATENT DOCUMENTS

| | | |
|---|---|---|
| CN | 1524507 A | 9/2004 |
| CN | 1234327 C | 1/2006 |
| CN | 101563113 A | 10/2009 |
| CN | 101938944 A | 1/2011 |
| CN | 202537562 U | 11/2012 |
| CN | 102946812 A | 2/2013 |
| CN | 104755033 A | 7/2015 |
| CN | 104825200 A | 8/2015 |
| EP | 1600108 A2 | 11/2005 |
| GB | 1401877 A | 8/1975 |
| JP | S4868094 A | 9/1973 |
| JP | S5223497 | 6/1977 |
| JP | S62243557 A | 10/1987 |
| JP | H07502913 A | 3/1995 |
| JP | 2001149485 A | 6/2001 |
| JP | 2005512678 A | 5/2005 |
| JP | 2005532134 A | 10/2005 |
| JP | 2010504835 A | 2/2010 |
| JP | 2013515417 A | 5/2013 |
| JP | 2013538603 A | 10/2013 |
| WO | WO-8401805 A1 | 5/1984 |
| WO | WO-9629013 A1 | 9/1996 |
| WO | WO-03053296 A1 | 7/2003 |
| WO | WO-2006124671 A2 | 11/2006 |
| WO | WO-2007004603 A1 | 1/2007 |
| WO | WO-2007044647 A2 | 4/2007 |
| WO | WO-2008019051 A2 | 2/2008 |
| WO | WO-2008060532 A2 | 5/2008 |
| WO | WO-2009066116 A1 | 5/2009 |
| WO | WO-2011019859 A2 | 2/2011 |
| WO | WO-2011019859 A3 | 4/2011 |
| WO | WO-2011043786 A1 | 4/2011 |
| WO | WO-2011139912 A1 | 11/2011 |
| WO | WO-2011159623 A1 | 12/2011 |
| WO | WO-2013067024 A1 | 5/2013 |
| WO | WO-2014066879 A2 | 5/2014 |
| WO | WO-2014070922 A1 | 5/2014 |
| WO | WO-2015012887 A1 | 1/2015 |
| WO | WO-2015103556 A1 | 7/2015 |
| WO | WO-2015168165 A1 | 11/2015 |
| WO | WO-2017027075 A1 | 2/2017 |
| WO | WO-2017044120 A1 | 3/2017 |
| WO | WO-2017181059 A1 | 10/2017 |
| WO | WO-2017184825 A1 | 10/2017 |
| WO | WO-2018081795 | 5/2018 |

OTHER PUBLICATIONS

"Notice of Allowance dated Jun. 20, 2018 for U.S. Appl. No. 15/130,764."

"Office action dated Jun. 6, 2018 for U.S. Appl. No. 15/201,088."

"Office action dated Nov. 2, 2018 for U.S. Appl. No. 15/442,382."

"PCT/US2017/059286 International Search Report and Written Opinion dated Mar. 6, 2018".

Thakral; et al., "Electrical stimulation to accelerate wound healing", CoAction, 2013, 4: 22061, 1-9.

"U.S. Appl. No. 14/958,803 Notice of Allowance dated Apr. 4, 2018".

U.S. Appl. No. 14/958,803 Notice of Allowance dated May 11, 2018.

"U.S. Appl. No. 14/851,059 Notice of Allowance dated Mar. 14, 2018".

Co-pending U.S. Appl. No. 15/081,526, filed Mar. 25, 2016.

Co-pending U.S. Appl. No. 15/081,550, filed Apr. 15, 2016.

Co-pending U.S. Appl. No. 15/096,083, filed Apr. 11, 2016.

Co-pending U.S. Appl. No. 15/130,764, filed Apr. 15, 2016.

Co-pending U.S. Appl. No. 15/337,768, filed Oct. 28, 2016.

Co-pending U.S. Appl. No. 15/369,293, filed Dec. 5, 2016.

"dictionary.com definition of "fixed", Available at http://www.dictionary.com/browse/fixed, accessed on Sep. 13, 2017".

(56) References Cited

OTHER PUBLICATIONS

European search report and opinion dated Jan. 7, 2014 for EP Application No. 11778067.6.
European search report and opinion dated Jan. 7, 2014 for EP Application No. 11796253.0.
"European search report and opinion dated Feb. 17, 2017 for EP Application No. 140829202."
"European search report and opinion dated Apr. 29, 2015 for EP Application No. 10822334.8."
European search report and opinion dated Jul. 12, 2016 for EP Application No. 13851258.
"European search report and written opinion dated Aug. 12, 2015 for EP Application No. 12844746.3."
European search report with written opinion dated Jul. 12, 2016 for EP13851258.
"Extended European search report and opinion dated Jul. 27, 2017 for EP Application No. 15733186".
Hasson, et al. A new sutureless technique for skin closure. Arch Surg. Jan. 1976 ;111(1):83-4.
"International search report and written opinion dated Jan. 12, 2016 for PCT Application No. US2015/049671."
International search report and written opinion dated Feb. 6, 2014 for PCT/US2013/067563.
International search report and written opinion dated Mar. 19, 2013 for PCT/US2012/062820.
"International search report and written opinion dated Apr. 29, 2015 for PCT/US2015/010188."
International search report and written opinion dated Jul. 29, 2011 for PCT/US2011/034649.
International search report and written opinion dated Jul. 30, 2010 for PCT/US2010/000430.
International search report and written opinion dated Aug. 30, 2016 for PCT/US2016/028297.
International search report and written opinion dated Sep. 10, 2014 for PCT/US2014/016587.
"International search report and written opinion dated Sep. 30, 2015 for PCT Application No. US2015/28066."
International search report and written opinion dated Oct. 21, 2011 for PCT Application No. US11/40213.
International search report with written opinion dated Jul. 14, 2017 for PCT/US2017/027695.
International search report with written opinion dated Jul. 18, 2017 for PCT/US2017/028537.
International search report with written opinion dated Aug. 30, 2016 for PCT/US2016/028297.
"K984204, 510(k) Premarket Notification Summary, Silverlon™ Direct Pressure Wound Closure Strip, May 19, 2007."
"Merriam-webster definition of "integral", accessed on Sep. 13, 2017, https://www.merriam-webster.com/dictionary/integral".
Merriam-Webster Dictionary. Definition of "lateral". Http://www.merriam-webster.com/dictionary/lateral. Accessed on May 5, 2016.
Notice of allowance dated Jan. 17, 2013 for U.S. Appl. No. 13/096,602.
Notice of allowance dated Feb. 10, 2015 for U.S. Appl. No. 14/180,524.
Notice of allowance dated Feb. 21, 2017 for U.S. Appl. No. 14/625,366.
Notice of allowance dated Feb. 23, 2016 for U.S. Appl. No. 15/081,595.
Notice of allowance dated Jun. 21, 2016 for U.S. Appl. No. 15/081,526.
Notice of allowance dated Sep. 17, 2012 for U.S. Appl. No. 13/286,378.
Notice of allowance dated Sep. 20, 2012 for U.S. Appl. No. 13/286,757.
"Notice of allowance dated Sep. 22, 2015 for U.S. Appl. No. 13/414,176."
Notice of allowance dated Sep. 30, 2016 for U.S. Appl. No. 15/130,149.
Notice of allowance dated Oct. 5, 2016 for U.S. Appl. No. 15/096,083.
Notice of allowance dated Oct. 14, 2016 for U.S. Appl. No. 15/081,550.
Notice of allowance dated Dec. 19, 2014 for U.S. Appl. No. 14/180,564.
Notice of allowance dated Dec. 19, 2016 for U.S. Appl. No. 15/130,149.
"Notice of Allowance dated Aug. 9, 2018 for U.S. Appl. No. 14/851,059."
Office action dated Feb. 1, 2017 for U.S. Appl. No. 15/130,764.
Office action dated Feb. 26, 2015 for U.S. Appl. No. 13/414,176.
Office action dated Mar. 4, 2016 for U.S. Appl. No. 13/874,046.
Office action dated Mar. 21, 2012 for U.S. Appl. No. 13/286,378.
Office action dated Mar. 21, 2014 for U.S. Appl. No. 13/414,176.
Office action dated Mar. 22, 2012 for U.S. Appl. No. 13/286,757.
"Office action dated Apr. 7, 2015 for U.S. Appl. No. 13/685,909."
Office action dated May 2, 2012 for U.S. Appl. No. 13/096,602.
Office action dated May 3, 2016 for U.S. Appl. No. 13/665,160.
Office action dated May 11, 2016 for U.S. Appl. No. 15/081,595.
Office action dated May 12, 2016 for U.S. Appl. No. 15/081,550.
Office action dated May 26, 2016 for U.S. Appl. No. 15/081,526.
Office action dated May 31, 2016 for U.S. Appl. No. 15/096,083.
"Office action dated Jun. 1, 2017 for U.S. Appl. No. 15/442,382."
"Office action dated Jun. 2, 2017 for U.S. Appl. No. 13/665,160."
"Office action dated Jun. 5, 2015 for U.S. Appl. No. 13/874,046."
Office action dated Jun. 17, 2014 for U.S. Appl. No. 13/414,176.
Office action dated Jun. 17, 2016 for U.S. Appl. No. 15/130,149.
Office action dated Jul. 20, 2016 for U.S. Appl. No. 15/130,764.
Office action dated Jul. 23, 2012 for U.S. Appl. No. 13/286,378.
Office action dated Jul. 23, 2012 for U.S. Appl. No. 13/286,757.
"Office action dated Jul. 27, 2017 for U.S. Appl. No. 14/851,059".
Office action dated Aug. 18, 2014 for U.S. Appl. No. 14/180,564.
"Office action dated Aug. 24, 2017 for U.S. Appl. No. 14/958,803".
Office action dated Aug. 28, 2014 for U.S. Appl. No. 14/180,524.
Office action dated Sep. 19, 2014 for U.S. Appl. No. 13/685,909.
"Office Action dated Sep. 22, 2017 for U.S. Appl. No. 13/665,160".
"Office Action dated Sep. 26, 2017 for U.S. Appl. No. 13/685,909".
"Office Action dated Oct. 5, 2017 for U.S. Appl. No. 14/958,818".
"Office action dated Oct. 14, 2015 for U.S. Appl. No. 13/685,909."
"Office action dated Oct. 23, 2015 for U.S. Appl. No. 13/665,160."
Office action dated Nov. 17, 2016 for U.S. Appl. No. 15/081,595.
Office action dated Nov. 19, 2012 for U.S. Appl. No. 13/096,602.
"Office Action dated Nov. 22, 2017 for U.S. Appl. No. 15/130,764".
"Office Action dated Nov. 28, 2017 for U.S. Appl. No. 15/442,382".
Office action dated Dec. 1, 2016 for U.S. Appl. No. 13/665,160.
Office action dated Dec. 29, 2014 for U.S. Appl. No. 13/685,909.
U.S. Appl. No. 13/681,825, filed Nov. 20, 2012.
U.S. Appl. No. 13/827,468, filed Mar. 14, 2013.
U.S. Appl. No. 13/096,602, filed Apr. 28, 2011.
U.S. Appl. No. 13/286,378, filed Nov. 1, 2011.
U.S. Appl. No. 13/286,757, filed Nov. 1, 2011.
U.S. Appl. No. 13/665,160, filed Oct. 31, 2012.
U.S. Appl. No. 13/685,909, filed Nov. 27, 2012.
U.S. Appl. No. 13/874,046, filed Apr. 30, 2013.
U.S. Appl. No. 14/180,524, filed Feb. 14, 2014.
U.S. Appl. No. 14/180,564, filed Feb. 14, 2014.
U.S. Appl. No. 14/625,366, filed Feb. 18, 2015.
"U.S. Appl. No. 13/685,909 Office Action dated May 1, 2018".
Zip@ Surgical Skin Closure. Fast, non-invasive alternative to staples, sutures and glue. Accessed Aug. 17, 2016. http://www.ziplinemedical.com/products/zip-surgical-skin-closure/.

* cited by examiner

METHODS AND APPARATUS FOR INHIBITING SCAR FORMATION

CROSS-REFERENCE TO RELATED APPLICATIONS

The present application is a divisional of U.S. patent application Ser. No. 13/685,909, filed on Nov. 27, 2012, which is a continuation of PCT Application No. PCT/US2011/040213, filed Jun. 13, 2011, which claims priority from provisional application No. 61/397,604, filed on Jun. 14, 2010, the full disclosures of which are incorporated herein by reference.

BACKGROUND OF THE INVENTION

1. Field of the Invention

Scarring is a natural response to the healing of wounds in a patient's skin. The wound healing process can be divided into three successive stages. A first inflammatory stage begins immediately after the injury which caused the wound. The inflammatory stage lasts up to a week during which time cellular processes remove damaged tissue and foreign matter from the wound. The inflammatory stage is followed by a proliferative stage which is characterized by fibroblast proliferation and the production of collagen and proteoglycans. The proliferative stage can last from days to weeks and is typically the stage during which hypertrophic scar formation begins, typically as a result of excess production of the extra cellular matrix which is synthesized to heal the wound. Such scars are referred to "hypertrophic scars." After the proliferative stage, a remodeling phase begins where the matrix which was produced in the proliferative is remodeled into an organized, cross-linked structure which increases the mechanical strength of the healed tissue.

Scars which are formed during the healing response are often treated after the healing is complete by cosmetics or surgical treatment. Cosmetic treatments are at best temporary solutions, and the need to have subsequent surgery is both inconvenient and a risk to the patient. It would therefore be desirable to provide methods and apparatus which could diminish scar formation during the healing process itself so that such subsequent procedures would be unnecessary or at least reduced in scope.

2. Description of the Background Art

WO/2011/019859 describes a device for inhibiting scarring in skin wounds, where the device is fixed to the skin and applies an outward force to spaced-apart skin locations. US2008/0069855 describes materials that will prevent scars and tissue adhesions. U.S. Pat. Nos. 7,511,185, 4,702,251, 4,539,990 and 4,535,772 describe wound healing devices that apply laterally inwardly opposed forces to the tissue on either side of the wound.

SUMMARY OF THE INVENTION

The present invention provides methods and apparatus for inhibiting scar formation during the healing of a wound on a skin surface. The term "scar" is intended includes not only common hypertrophic scars which occurs from cuts, abrasions, and the like, but also to include keloids which are hyperplastic masses that occur in the dermis and adjacent subcutaneous tissue in certain individuals, typically following trauma.

The methods and apparatus of the present invention treat healing wounds by applying a downward force on the wound while simultaneously applying a compression force in order to relieve tension in the tissue across or surrounding the wound, usually during the proliferative and/or remodeling stages of the wound healing process. Treatment during the late portions of the inflammatory stage might also be useful, and in some instances treatment after remodeling might also be performed. For example, simultaneous downward compression and lateral compression may applied to the wound at or near the end of the inflammatory stage, typically at a time in the range form 1 day to 30 days after the wound occurred and first began to heal. After commencing treatment, the forces may continue to be applied for a period of time in the range from one day to 21 days, or longer, and the forces may be increased, decreased, or held constant during the treatment period.

Apparatus according to the present invention are specially adapted to provide such simultaneous downward and lateral compressive forces to the region of the wound in the skin, typically comprising a tissue displacement device which can placed on the skin surface to cover the wound itself as well as some distance lateral to the wound, typically from several millimeters to one or two centimeters or more on each side of the wound. The tissue displacement device may be actuated to apply the desired vertically downward force in a variety of ways as described below.

The apparatus of the present invention will also typically include a backing which can be secured to the skin on either side of the healing wound, where the backing is typically adapted to draw the skin surface and underlying tissue layers laterally inwardly to provide the desired lateral compression and in turn relieve tension in the tissue. In the described embodiments, the inward lateral movement of the skin and underlying tissue will be effected by raising a center of the backing (after the backing has been applied to the skin surface), usually as a result of actuating the tissue displacement device, to draw the sides of the backing laterally inwardly.

The backing may comprise a strip or layer of material which can be attached to the skin over the tissue displacement device, with lateral regions of the backing adhering to the skin surface on opposite sides of displacement device. Usually at least the lateral portions of the backing will be non-distensible (resistant to stretching or inelastic), and more usually the entire backing will have limited stretchability or elasticity, often being entirely non-distensible. By non-distensible, it is meant that the backing material will have an elongation at break of less of less than 20%, typically less than 15%, and often less than 10%. Alternatively, the backing may comprise a strap or other longer structure which can be wrapped around a patient's limb in order to constrain the tissue displacement device on the skin surface above below.

In the exemplary embodiments, the tissue displacement device comprises a balloon or other expandable device having a relatively non-distensible bottom surface which is disposed against the wound and a relatively distensible top surface which inflates upwardly to raise a central region of the backing which in turn causes the lateral portions of the backing to draw laterally inwardly to provide the desired inward tissue compression.

In order to treat long wounds covering five centimeters, ten centimeters, twenty centimeters, or longer, the apparatus of the present invention can be formed in segments, each usually comprising a separate backing and a separate tissue compression device as described previously. The segments will be linked together by flexible joints, links or other components which allow the resulting assembly to conform to a skin surface and follow irregular topology of the wound and skin. The resulting "flexibility" is also useful in allowing the assembly to conform to the skin surface when the patient moves or is moved by others. In some embodiments, the joints will be formed as short tubes or other structures capable of delivering an inflation medium to each successive segment from either end of the assembly.

Still other apparatus could be constructed in accordance with the principles of the present invention. For example, for localized wounds, a circular, stretchable elastic backing having an adhesive surface for adhering to the skin could be provided. By initially stretching the elastic backing radially outwardly, for example using a constraining frame or other component, the elastic backing could be placed over the wound and released from its constraint to apply the literally inward force to the wound. A variety of tissue compression devices can be placed under or over the backing in order to provide the vertical compression desired.

Still alternative, apparatus could be provided including a more rigid disk having an adhesive on an outer annular surface and a center portion free from the adhesive that can be everted or otherwise deformed to press inwardly against tissue and draw the annular circumference of the disk inwardly to provide simultaneous radial compression and vertical force. For example, the center portion could "snap" from an everted configuration to an inverted configuration much like a bottle top with an indication that the top has been previously opened.

In still other embodiments, a lower of other surface of the tissue displacement device may be coated with a drug to deliver that drug to the skin during the treatment.

DETAILED DESCRIPTION OF THE INVENTION

Figure 1:
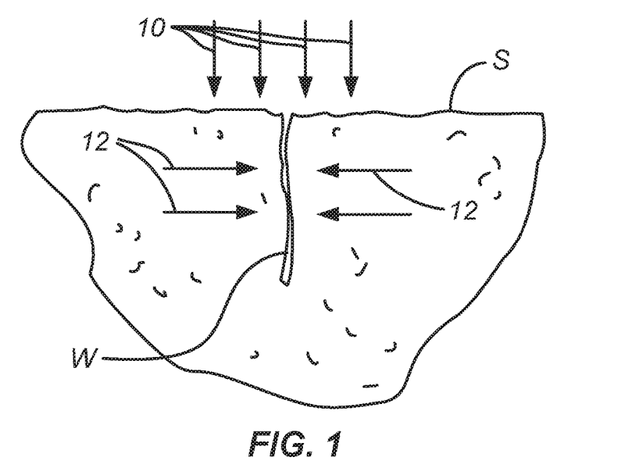
FIG. 1 is a schematic illustration of a wound showing vertical and lateral force compression applied in accordance with the principles of the present invention.

FIG. 1 is a schematic diagram illustrating a subcutaneous wound W in a skin surface S where the wound extends some distance beneath the surface. To reduce scarring as the wound heals in accordance with the principles of the present invention, a downward or vertical force will be applied over a region spanning the wound and extending from several millimeters to several centimeters or longer onto the skin surface from each side of the wound as generally indicated by the vertical arrows 10. Pressure is preferably applied along most or all of the length of elongated. The cuts, incisions, and other elongated wounds that are treated by the present invention will typically extend into the dermis by several millimeters or more. In addition to the vertical force, present of the invention will provide a compressive force or pressure indicated by arrows 12 preferably extending from the surface down to a depth close to or equal to the depth of the wound.

Figure 2:
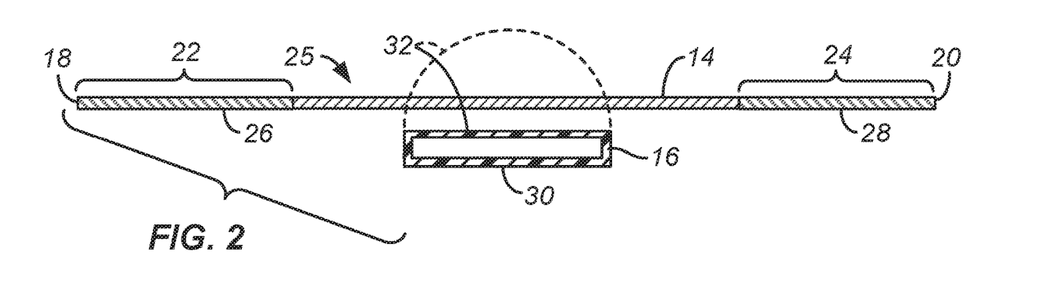
FIGS. 2, 2A and 2B illustrate a first apparatus and its use for applying such vertical and lateral force compression.

Methods of the present invention for applying the forces illustrated in FIG. 1 can be performed using a variety of apparatus. One exemplary apparatus is illustrated in FIG. 2 and includes both a backing 14 and a tissue displacement device 16 which can be assembled and used in combination for applying the desired forces. The backing 16 will usually be non-distensible over most or all of its length from end 18 to end 20. The length will usually be in the range from 5 centimeters to 10 centimeters, 20 centimeters, or longer. The width will typically be in the range from 1 centimeter to 5 centimeters. Backing will be divided into regions, including a first lateral region 22 and a second lateral region 24. At least a portion of each of these lateral regions will be substantially non-distensible and they will have adhesive surfaces 26 and 28 which can be applied to the skin to hold the backing in place. A central region 14 of the backing between the lateral regions 22 and 24 may have some ability to stretch (distensibility), but the central region will also typically be non-distensible over all or a portion of its length. The bottom surface of this central region of the backing, however, will be usually free from all adhesives so that the central region may be placed over the tissue displacement device 16 with the central region able to move over the top of the displacement device as the displacement device is expanded as shown in broken line in FIG. 2. The displacement device 16 will typically be formed from an elastic material over its upper portions to allow the desired vertical expansion while a bottom or base 30 of the device 16 resists expansion. Thus, the upper surface 32 which is elastic can expand to the extent shown in broken line when the device is actuated. Usually, the tissue displacement device 16 will be an inflatable structure, such as a balloon, where the thickness of and/or reinforcement within the bottom of the structure resists stretching and the upper portion is elastic to allow expansion upon inflation of the structure. In other cases, a balloon or other inflatable of expandable structure with a round or elliptical profile could be used.

Figure 2A:
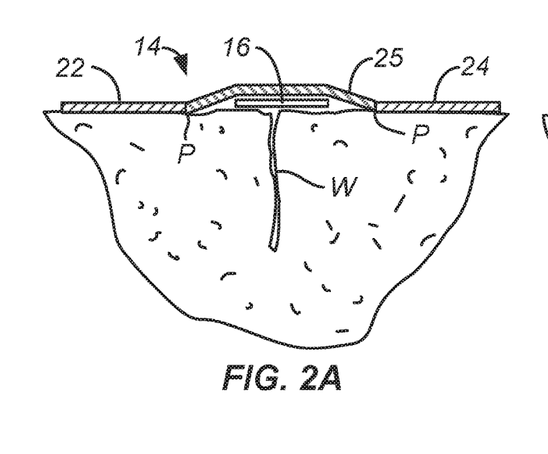
Figure 2B:
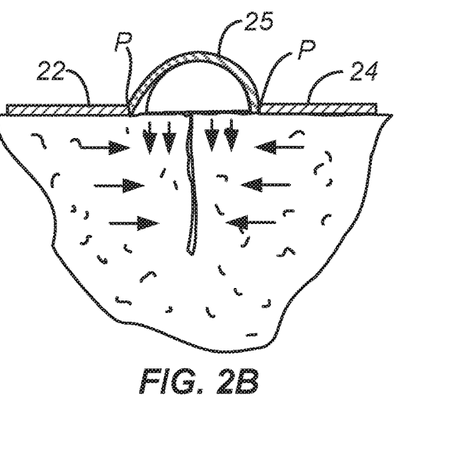

In use, the assembly of FIG. 2 is placed over a wound so that the lateral regions 22 and 24 of the backing 14 adhere to the skin's surface on opposite sides of the wound W. The tissue displacement device 16 is held directly over the wound W by the central section of the backing as shown in FIG. 2A. As shown in FIGS. 2A and 2B, the bottom or base 30 of the tissue displacement device 16 may be wider than the healing wound W to laterally span the healing wound W in the transverse direction. The tissue displacement device 16 may then be inflated to raise the central section and as shown in FIG. 2B. By raising the central section 25, the lateral portions 22 and 24 are drawn laterally inward to compress the upper surface of the tissue which in turn compresses the tissue on either side of the wound at the lower depths as shown by the arrows in FIG. 2B. Simultaneously, the bottom or base 30 of the tissue displacement device applies a downward pressure over the wound as indicated by the vertical arrows in FIG. 2B. As shown in FIG. 2A and FIG. 2B, the bottom or base 30 of the tissue displacement device 16 may be flat and remain flat upon inflation of the structure, thereby providing a uniform downward pressure. The asymmetric structure of the tissue displacement device allows this selective application of forces to achieve the objectives of the present invention. Each of the lateral portions 22 and 24 will be attached on the skin surface up to a point P. the backing will be unattached to the skin between point P and area covered by the tissue displacement device 16. It is this short unattached region of the backing which allows the lateral portions 22 and 24 to be drawn inwardly without significantly pulling the skin upwardly, as shown in FIG. 2B.

Figure 3:
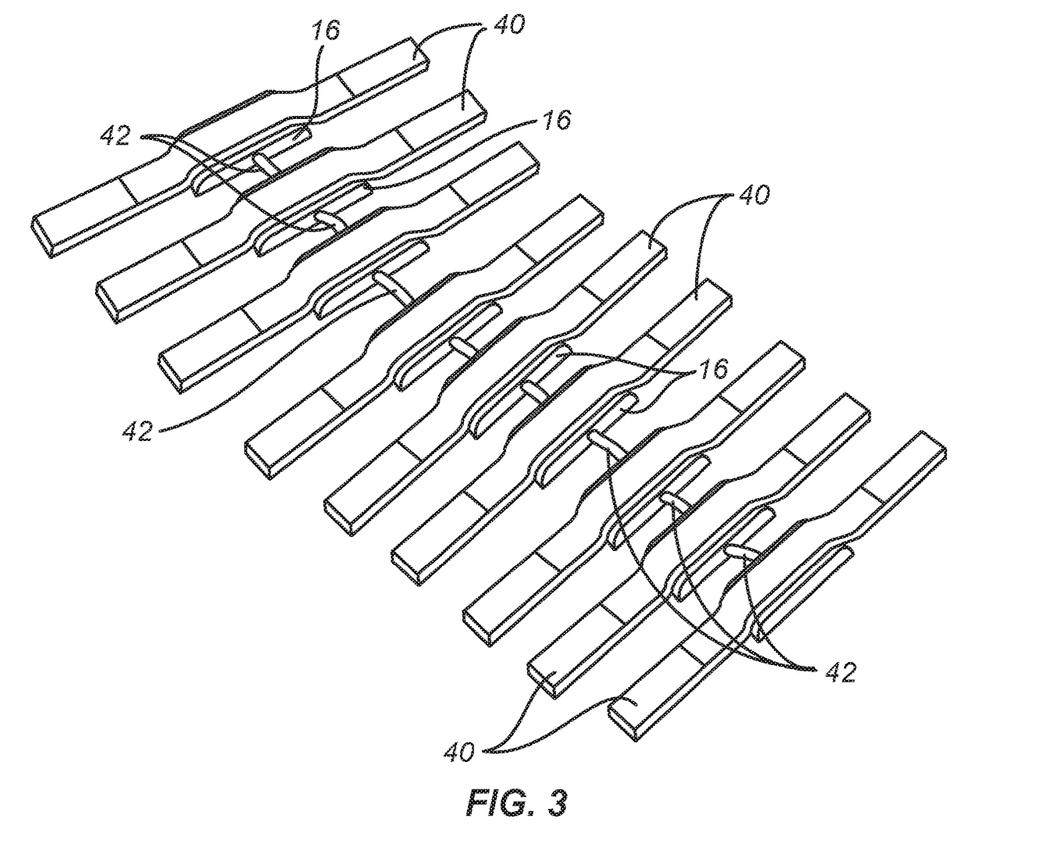
FIG. 3 illustrates a segmented assembly constructed in accordance with the principles of the present invention which can be used for treating elongated or irregular wounds.

In order to treat lengthy wounds, the apparatus as generally shown in FIG. 2, can be formed in multiple segments 40, as illustrated in FIG. 3. Each segment 40 will generally have the structure illustrated in FIG. 2, and adjacent segments will be joined by short tubular connectors of links 42 which both hold the segments together and which permit simultaneous inflation of each of the tissue displacement devices 16. The segmented structure of FIG. 3 is advantageous since it permits the assembly to follow non-linear wounds and also allows the assembly to conform to the tissue surface as the patient moves or is moved during the scar treatment.

Figure 4:
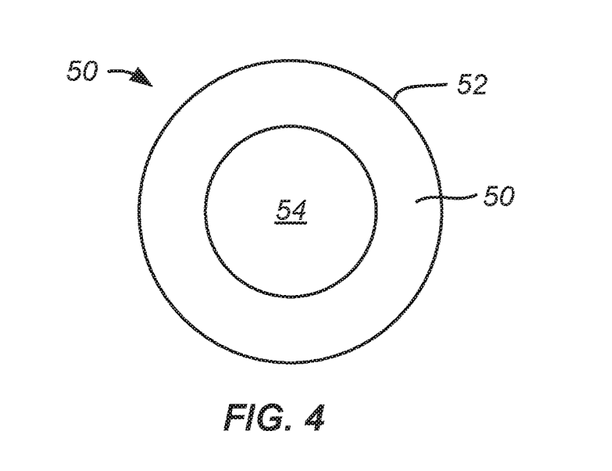
FIG. 4 illustrates an alternative apparatus for treating wounds in accordance with the principles of the present invention.
Figure 5A:
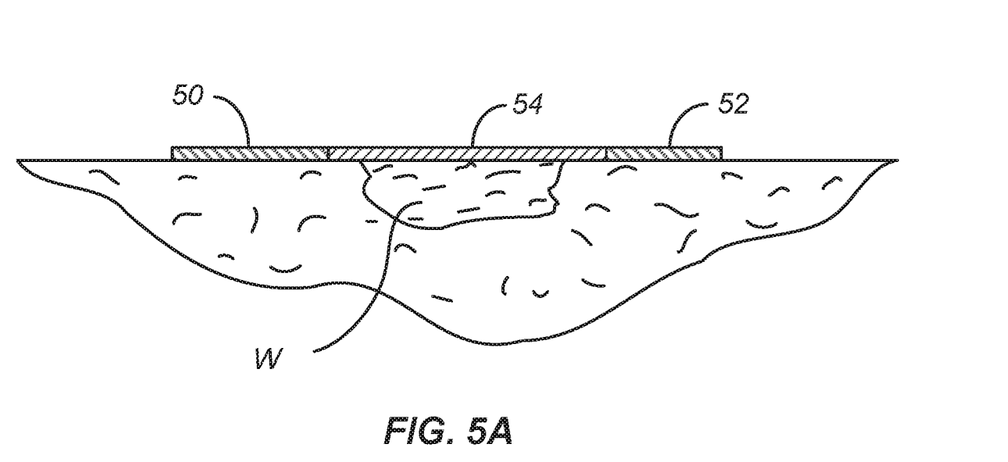
FIGS. 5A and 5B illustrate use of the apparatus of FIG. 4 in treating a localized wound.
Figure 5B:
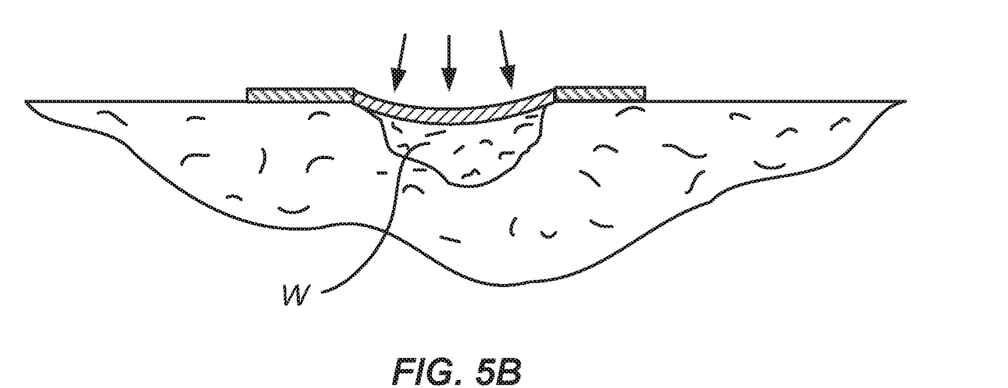

An alternative treatment device 50 is illustrated in FIG. 4. The device comprises a backing 52 having an outer annular portion 54 which has an adhesive surface for attachment to the patient's skin. The device 50 further includes a central section 54 which can be everted or depressed in order to both apply vertical force to a wound and simultaneously apply radially inward forces, as illustrated in FIGS. 5A and 5B. Such an evertable central section could also be used with the elongated or strip-like devices described previously.

As shown in those FIGS. 5A and 5B, a localized (non-elongated) wound W may be covered by the central portion 54 of the device 50 while the annular portion 52 adheres to the skin surrounding the wound. By then deforming and depressing the center section 54 and shown in FIG. 5B, a vertical force is applied over the wound while simultaneously the annular portion 52, which will typically be elastic, is drawn inwardly to radially compress the tissue about the wound.

What is claimed is:

1. A method for inhibiting scar formation in a healing wound on a skin surface, said method comprising:
    positioning a tissue displacement device on a skin surface such that the tissue displacement device covers (i) the healing wound, (ii) a first portion of the skin surface that is lateral to the healing wound on a first side of the healing wound, and (iii) a second portion of the skin surface that is lateral to the healing wound on a second side of the healing wound;
    securing a backing to the skin surface on the first side of the healing wound and the second side of the healing wound such that the backing extends over the tissue displacement device; and
    after securing the backing to the skin surface, applying a downward force on the healing wound, the first portion of the skin surface, and the second portion of the skin surface while simultaneously applying a lateral compression force to tissue across the healing wound by:
        expanding the tissue displacement device to cause the tissue displacement device to apply the downward force on the healing wound, the first portion of the skin surface, and the second portion of the skin surface, and
        raising, by the tissue displacement device expanding against the backing, a center of the backing to draw opposing sides of the backing laterally inward toward each other and apply the lateral compression force to the tissue.

2. The method of claim 1, wherein the backing comprises (i) a first lateral region that is secured to the skin surface on the first side of the healing wound, (ii) a second lateral region that is secured to the skin surface on the second side of the healing wound, and (iii) a central region between the first lateral region and the second lateral region.

3. The method of claim 2, wherein the first lateral region and the second lateral region are non-distensible.

4. The method of claim 2, wherein the first lateral region of the backing comprises a first adhesive surface and the second lateral region of the backing comprises a second adhesive surface, and
    wherein securing the backing to the skin surface comprises:
        adhering, using the first adhesive surface, the first lateral region of the backing to the skin surface on the first side of the healing wound, and
        adhering, using the second adhesive surface, the second lateral region of the backing to the second side of the healing wound.

5. The method of claim 2, wherein the central region of the backing is free of adhesive such that the central region of the backing moves relative to the tissue displacement device while expanding the tissue displacement device.

6. The method of claim 2, wherein expanding the tissue displacement device to cause the tissue displacement device to apply the downward force on the healing wound comprises engaging the tissue displacement device with the central region of the backing.

7. The method of claim 2, wherein the central region has a surface area that is wider than the healing wound.

8. The method of claim 1, wherein applying the downward force on the healing wound while simultaneously applying the lateral compression force is performed at a time beginning from 1 day to 30 days after the healing wound began to heal.

9. The method of claim 8, wherein applying the downward force on the healing wound while simultaneously applying the lateral compression force is performed for a period of time in the range from 1 day to 21 days.

10. The method of claim 9, further comprising increasing an amount of the downward force and an amount of the lateral compression force at least once during said period of time.

11. The method of claim 9, further comprising decreasing an amount of the downward force and an amount of the lateral compression force at least once during said period of time.

12. The method of claim 1, wherein the tissue displacement device comprises an inflatable balloon having a relatively non-distensible bottom surface which is applied against the healing wound and a relatively distensible top surface which inflates upwardly away from the non-distensible bottom surface to raise the backing.

13. The method of claim 12, wherein the relatively non-distensible bottom surface is a flat surface when the tissue displacement device is expanded.

14. The method of claim 12, wherein the tissue displacement device has a D-shaped profile when expanded.

15. The method of claim 12, wherein the relatively non-distensible bottom surface is coated with a drug.

16. The method of claim 1, wherein the healing wound is elongated in a direction,
    wherein the tissue displacement device comprises a plurality of segments coupled to each other, wherein the plurality of segments are axially displaceable relative to each other along the direction in which the healing wound is elongated.

17. The method of claim 16, wherein the plurality of segments are coupled to each other by a plurality of flexible links.

18. The method of claim 17, further comprising delivering, via the plurality of flexible links, an inflation medium to each successive segment of the tissue displacement device from one end of the tissue displacement device.

19. The method of claim 16, wherein the backing comprises a plurality of backing segments, and wherein each backing segment covers a respective segment of the tissue displacement device.

20. The method of claim 1, wherein securing a backing to the skin surface on the first side of the healing wound and the second side of the healing wound comprises wrapping the backing around one anatomical structure selected from a group consisting of: a limb, a torso, and an abdomen.

* * * * *